United States Patent [19]

Guiducci et al.

[11] Patent Number: 4,742,176
[45] Date of Patent: May 3, 1988

[54] PROCESS FOR 2-[(2-CHLOROPHENYL)METHYL]-4,4-DIMETHYL-3-ISOXAZOLIDINONE

[75] Inventors: Mariano A. Guiducci, Edison; Matthew I. Levinson, East Brunswick, both of N.J.

[73] Assignee: FMC Corporation, Philadelphia, Pa.

[21] Appl. No.: 829,337

[22] Filed: Feb. 14, 1986

[51] Int. Cl.⁴ .................................... C07D 263/08
[52] U.S. Cl. ........................ 548/243; 260/500.5 H; 540/355
[58] Field of Search ............ 548/243; 540/355; 260/500.5 H

[56] References Cited

U.S. PATENT DOCUMENTS

| | | | |
|---|---|---|---|
| 2,862,001 | 11/1958 | Kirchensteiner et al. | 260/500.5 H |
| 3,271,415 | 9/1966 | van der Burg | 260/500.5 H |
| 3,364,110 | 1/1968 | Lehr et al. | 260/500.5 H |
| 3,475,485 | 10/1969 | Davis | 260/500.5 H |
| 4,337,197 | 6/1982 | Gordon | 540/355 |
| 4,405,357 | 9/1983 | Chang | 548/243 |
| 4,455,430 | 6/1984 | Kelly et al. | 548/243 |

OTHER PUBLICATIONS

Chemical & Engineering News, Jul. 7, 1986, pp. 7–8.
Bauer et al., *Angew. Chem.* International Edition, 13, 376 (1974).
Hughes et al., *J. Chem. Soc.*, 164 (1971).
W. P. Jencks, *J. Am. Chem. Soc.*, 80, 4581 (1958).
W. P. Jencks, *J. Am. Chem. Soc.*, 80, 4585 (1958).
W. P. Jencks et al., *Biochemistry*, 2, 1313 (1963).
J. W. Munson, "Chemistry and Biology of Hydroxamic Acids," S. Karger AG, Basil, Switzerland, 1982, pp. 1–13.
Katritzky et al., "Advances in Heterocyclic Chemistry," vol. 10, Academic Press, New York, 1969, pp. 199–241.
J. M. Lawlor, *Chem. Comm.*, 404 (1967).
Moews, Jr., et al., *J. Inorg. Nucl. Chem.*, 11, 242 (1959).
Nicolaus et al., *Gass. Itl. Chem.*, 93, 618 (1963) (w/translation).

*Primary Examiner*—Donald G. Daus
*Assistant Examiner*—E. Bernhardt
*Attorney, Agent, or Firm*—William Schmonsees; Richard L. Hansen; H. Robinson Ertelt

[57] ABSTRACT

An improved process for the manufacture of herbicidal 2-[(2-chlorophenyl)methyl]-4,4-dimethyl-3-isoxazolidinone by cyclizing 3-chloro-N-hydroxy-2,2-dimethylpropanamide with an alkaline or alkaline earth hydroxide at a pH of 7.5 to 9.5, benzylating the resulting 4,4-dimethyl-3-isoxazolidinone, eliminating by-product 1-[(2-chlorophenyl)methoxy]-3,3-dimethyl-2-azetidinone by contacting the product mixture with anhydrous hydrogen chloride, and further benzylating free isoxazolidinone with base.

5 Claims, No Drawings

PROCESS FOR 2-[(2-CHLOROPHENYL)METHYL]-4,4-DIMETHYL-3-ISOXAZOLIDINONE

This invention is in the field of heterocyclic organic chemistry; more specifically, it relates to heterocyclic compounds containing nitrogen and oxygen atoms, especially the five-membered heterocycle known as isoxazolidinone and processes for manufacturing such compounds.

2-[(2-chlorophenyl)methyl]-4,4-dimethyl-3-isoxazolidinone is disclosed in U.S. Pat. No. 4,405,357 and its herbicidal properties are described. This herbicidal isoxazolidinone is represented by the following structural formula:

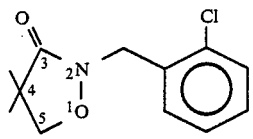

The aforesaid patent discloses two methods by which the herbicidal isoxazolidinone can be prepared. Both methods require the cyclization with base of a chloro-substituted N-hydroxy-2,2-dimethylpropanamide. In one method the N-(2-chlorophenyl)methyl moiety is carried through the cyclization; in the other method the N-(2-chlorophenyl)methyl moiety is added by alkylation following cyclization. This latter process is represented ideally by the following sequence of reactions:

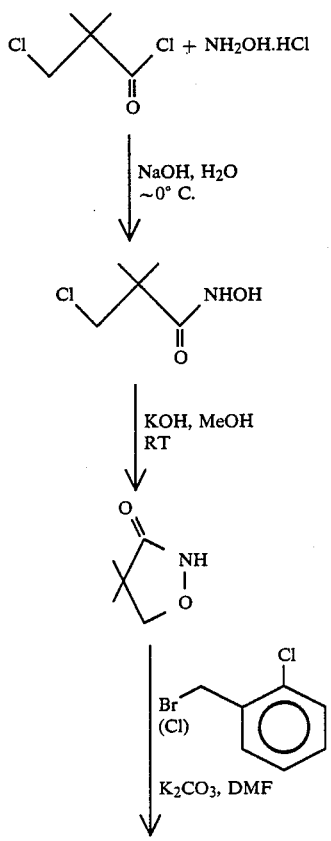

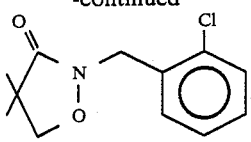

In carrying out this process on a commerical scale it is advantageous to combine the last two steps, avoiding isolation of the intermediate cyclization product, 4,4-diemthyl-3-isoxazolindinone. When this is done, it is found the final, herbicide product I is contaminated with 3-[(2-chlorophenyl)methoxy]-4,5-dihydro-4,4-dimethylisoxazole and 1-[(2-chlorophenyl)methoxy]-3,3-dimethyl-2-azetidinone, structures II and III, respectively.

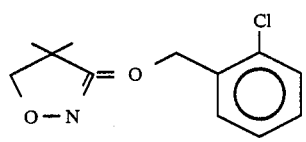

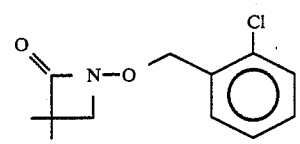

A typical product mixture will include I:II:III in the ratio of about 85/10/5.

The instant invention represents an improvement of this process, especially as to treatment of the product mixture, increasing the yield and the purity of the final herbicidal product. Briefly, the improvement comprises contacting the product mixture with anhydrous hydrogen chloride gas prior to isolating the desired product. This treatment converts by-product II into a mixture of 4,4-dimethyl-3-isoxazolidinone and 2-chlorobenzyl chloride, which can be recycled with base to the desired herbicide product. By-product III is converted into readily separated components, and the desired product I is unaffected by contact with HCl gas. Other aspects of the improvement include careful control of the pH in the process stage requiring base.

The improvements introduced by this invention will be clarified by reference to the following Examples:

EXAMPLE 1

3-Chloro-N-hydroxyl-2,2-dimethylpropanamide

A two liter resin kettle was equipped with two inlet tubes, a thermometer, stirring paddle, pH probes and a cooling jacket. A solution of hydroxylamine sulfate (264 g, 1.61 moles) and ethyl xanthic acid, potassium salt (0.5 g, 0.003 mole) in 700 ml of water was added to the kettle and the stirrer started. One of the inlet tubes was connected through a metering pump to a reservoir containing an aqueous 50% sodium hydroxide solution. The addition of base to the reaction mixture was regulated by an electronic pH meter/controller connected to the pump and pH probe and set for pH of 7.2. Aqueous base was delivered to the reactor until that pH was attained. The other inlet tube was connected through a metering pump to a reservoir containing 3-chloro-2,2-dimethyl-propionyl chloride (286 g, 1.84 moles). The acid chloride was added to the reaction mixture during a period of 2.5 hours at a temperatue of 28° C., maintaining a pH of 7.2 by simultaneous addition of base. The reaction slurry was then vacuum filtered and the filter cake dried. The dried filter cake weighted 293 g. An aliquot of the filter cake was dissolved in a mixture of DMF and toluene. Analysis of the extract using GLPC indicated the yield of 3-chloro-N-hydroxy-2,2-dimethylpropanamide, based on the amount of 3-chloro-2,2-dimethylpropionyl chloride, was 85%.

The ph of the reaction mixture should be maintained in the 7.0–7.5 range for best results. The reaction is readily adapted for continuous processing using techniques known to those skilled in the art.

EXAMPLE 2

4,4-Dimethyl-3-isoxazolidinone

A five liter three-necked round bottom flask was equipped with an inlet tube, thermometer, stirring paddle, pH probe and a heating mantle. The reaction flask was charged with 996.0 g of a mixture prepared by the method of Example 1 and containing 73.0% by weight 3-chloro-N-hydroxy-2,2-dimethylpropanamide (4.80 moles) and 2,670 ml of water. The inlet tube was connected through a metering pump to a reservoir containing an aqeuous 50% sodium hydroxide solution. Addition of base to the stirred reaction mixture was regulated by an electronic pH meter/controller connected to the pump and pH probe. The pH meter/controller was set to control the pH at 8.8±0.1, and the pump was started. The reaction mixture was stirred at 36° C. to 45° C. for three hours until additional base was no longer required to maintain the pH. At the end of the three hour period 25.6 g (0.24 mole) of sodium carbonate was added. The resultant mixture was allowed to cool to room temperature and stirred for approximately 18 hours.

The pH during this reaction should be maintained in the range 7.5–9.5, preferably 8.5–9.5. The nature of the base is not critical, as long as it is not otherwise reactive with the components of the mixture. The reaction can be carried out in the range 25°–60° C., preferably 30°–50° C..

EXAMPLE 3

2-[(2-Chlorophenyl)methyl]-4,4-dimethyl-3-isoxazolidinone

Without isolating the product from Example 2, the reaction solution was heated at 85° C. and a solution of 39.6 g (0.098 mole) of tricaprylylmethylammonium chloride in 789.0 g (4.90 moles) of 2-chlorobenzyl chloride was added slowly. After the addition was completed the reaction mixture was stirred at 85° C. for five hours. The mixture was cooled, and the organic phase (1195.5 g) was separated from the aqueous phase and saved. The aqueous phase was extracted with methylene chloride. The solvent was evaporated from the extract under reduced pressure leaving an oil (11.3 g). This oil was combined with the organic phase for a total of 1206.8 g. Gas-liquid phase chromatographic analysis (GLPC) of this oil indicated 87.1% by weight 2-[(2-chlorophenyl)methyl]-4,4-dimethyl-3-isoxazolidinone and 3-[(2-chlorophenyl)methoxy]-4,5-dihydro-4,4-dimethylisoxazole (a combined yield of 91.4% based on 3-chloro-N-hydroxy-2,2-dimethylpropanamide), 1.0% by weight 2-chlorobenzyl chloride, and 4.2% by weight 1-[(2-chlorophenyl)methoxy]-3,3-dimethyl-2-azetidinone (a yield of 4.7% based on 3-chloro-N-hydroxy-2,2-dimethylpropanamide). The remaining 7.7% contained a number of by-products each of which was less than 1%.

Anhydrous hydrogen chloride gas (53.0 g, 1.54 mole) was bubbled into 1164.9 g of the aforesaid oily mixture. In the general case, it is important that the reaction mixture be anhydrous for optimum yield of the desired product. This mixture was heated at 45° C. and stirred for three hours. The mixture was cooled, and 116.0 g of an aqueous 50% sodium hydroxide solution was added in order to neutralize the reaction mixture and raise the pH to 8.5. After stirring for a brief period, 15.0 g (0.14 mole) of sodium carbonate was added. This mixture was stirred and heated at 85° C. for 2.5 hours, maintaining a pH of 8.5–9.5. The hot reaction mixture was washed with two 1,000 ml portions of hot (90° C.) water. The remaining organic solution was dried under reduced pressure, yielding 1155.0 g of a liquid. GLPC analysis of this liquid indicated 86.6% by weight 2-[(2-chlorphenyl)methyl]-4,4-dimethyl-3-isoxazolidinone and 2-[(2-chlorophenyl)methoxy]-4,5-dihydro-4,4-dimethylisoxazole (a combined 98.2% recovery) and 0.5% by weight 2-chlorobenzyl chloride. There was no detectable 1-[(2-chlorphenylmethoxy]-3,3-dimethyl-2-axetidinone. The remaining 12.9% consisted of a number of by-products, each of which was 1% or less.

What is claimed is:

1. A process for preparing an N-benzyl substituted isoxazolidinone, substantially free of azetidinone, which comprises
    (i) cyclizing a 3-chloro-N-hydroxypropanamide with a base selected from alkaline and alkaline earth hydroxides, while maintaining the pH in a range of 7.5 to 9.5;
    (ii) reacting the unisolated products of step i with a benzyl halide;
    (iii) isolating and dehydrating the non-aqueous phase products from the products of step ii;
    (iv) treating the products of step iii with at least 0.2 mole of anhydrous hydrogen chloride per mole of propanamide; and
    (v) continuously treating the unisolated products of step iv with sufficient base, selected from alkaline and alkaline earth hydroxides and carbonates, to maintain the pH in a range of 7.5 to 9.5, for a period of one to three hours.

2. A process of claim 1 in which the benzyl halide is 2-chlorobenzyl chloride.

3. A process of claim 1 in which the pH in step i is maintained in the range of 8.5 to 9.5.

4. A process of claim 1 in which the 3-chloro-N-hydroxypropanamide is 3-chloro-n-hydroxy-2,2-dimethylpropanamide.

5. A process for preapring 2-[(2-chlorophenyl)methyl]-4,4-dimethyl-3-isoxazolidinone which comprises,
    (i) cyclizing 3-chloro-N-hydroxy-2,2-dimethylpropanamide with sodium hydroxide, while maintaining the pH in a range of 7.5 to 9.5;
    (ii) reacting the unisolated products of step i with 2-chlorobenzyl chloride;
    (iii) isolating and dehydrating the non-aqueous phase products from the products of step ii;
    (iv) treating the product of step iii with anhydrous hydrogen chloride; and
    (v) continuously treating the unisolated products of step iv, with sufficient base selected from sodium carbonate and sodium hydroxide to maintain the pH in a range of 7.5 to 9.5, for a period of one to three hours.

* * * * *